United States Patent
Choi et al.

(10) Patent No.: US 10,311,602 B2
(45) Date of Patent: Jun. 4, 2019

(54) COMPUTED TOMOGRAPHY DEVICE AND COMPUTED TOMOGRAPHY IMAGE CORRECTION METHOD USING THE SAME

(71) Applicant: ELECTRONICS AND TELECOMMUNICATIONS RESEARCH INSTITUTE, Daejeon (KR)

(72) Inventors: Jang Hwan Choi, Daejeon (KR); SooYeul Lee, Daejeon (KR)

(73) Assignee: ELECTRONICS & TELECOMMUNICATIONS RESEARCH INSTITUT, Daejeon (KR)

(*) Notice: Subject to any disclaimer, the term of this patent is extended or adjusted under 35 U.S.C. 154(b) by 94 days.

(21) Appl. No.: 15/683,043

(22) Filed: Aug. 22, 2017

(65) Prior Publication Data
US 2018/0197315 A1  Jul. 12, 2018

(30) Foreign Application Priority Data
Jan. 9, 2017  (KR) .................. 10-2017-0003061

(51) Int. Cl.
*G06K 9/00* (2006.01)
*G06T 11/00* (2006.01)
(Continued)

(52) U.S. Cl.
CPC ............ *G06T 11/005* (2013.01); *A61B 6/032* (2013.01); *A61B 6/4429* (2013.01);
(Continued)

(58) Field of Classification Search
None
See application file for complete search history.

(56) References Cited

U.S. PATENT DOCUMENTS 5,414,623 A * 5/1995 Lu .................. G06T 11/006
                                                    382/131
5,442,674 A   8/1995 Picard et al.
(Continued)

FOREIGN PATENT DOCUMENTS

JP     2009-082320 A   4/2009
KR  10-2004-0111005 A  12/2004

OTHER PUBLICATIONS

Youngbin Cho et al., "Accurate technique for complete geometric calibration of cone-beam computed tomography systems", Medical Physics, Mar. 18, 2005, pp. 968-983, vol. 32, No. 4, American Association of Physicists in Medicine.
(Continued)

*Primary Examiner* — Shervin K Nakhjavan

(57) ABSTRACT

Provided are a computed tomography device and a computed tomography method. The computed tomography device includes a gantry and an image processing processor. The gantry includes a light source for irradiating light, a detector disposed facing the light source and for receiving the light, and an arm for supporting the light source and the detector. The image processing processor receives a two-dimensional detection image for a subject from the detector. The image processing processor converts the received two-dimensional detection image to two-dimensional detection image data. The image processing processor generates three-dimensional reconstruction image data from the two-dimensional detection image data. A computed tomography device and a computed tomography method according to the inventive concept correct an error of a gantry movement path to provide a stable three-dimensional reconstruction image.

20 Claims, 9 Drawing Sheets

(51) Int. Cl.
*A61B 6/03* (2006.01)
*A61B 6/00* (2006.01)

(52) U.S. Cl.
CPC .......... *A61B 6/5205* (2013.01); *G06T 11/006* (2013.01); *A61B 6/4405* (2013.01); *A61B 6/4441* (2013.01); *A61B 6/54* (2013.01); *G06T 2211/40* (2013.01)

(56) References Cited

U.S. PATENT DOCUMENTS

| | | | |
|---|---|---|---|
| 7,186,023 | B2 | 3/2007 | Morita et al. |
| 8,666,133 | B2 | 3/2014 | Vermandel et al. |
| 9,099,280 | B2 | 8/2015 | Jeong et al. |
| 9,390,825 | B2 | 7/2016 | Lee et al. |
| 2001/0053204 | A1 | 12/2001 | Navab et al. |
| 2008/0080758 | A1* | 4/2008 | Hoppe ............... A61B 6/583 382/132 |
| 2010/0266178 | A1* | 10/2010 | Liang ............... G06T 11/006 382/131 |
| 2011/0123081 | A1* | 5/2011 | Sebok ............... A61B 6/032 382/131 |
| 2011/0160571 | A1* | 6/2011 | Cohen ............... A61B 5/06 600/424 |
| 2014/0133722 | A1* | 5/2014 | Lee ............... G06T 5/003 382/131 |
| 2015/0125033 | A1* | 5/2015 | Murphy ............... G06T 7/251 382/103 |
| 2015/0138186 | A1* | 5/2015 | Carrell ............... F24C 15/2021 345/419 |
| 2018/0182128 | A1* | 6/2018 | Champley ............. G06T 11/006 |

OTHER PUBLICATIONS

M. J. Daly et al., "Geometric calibration of a mobile C-arm for intraoperative cone-beam CT", Medical Physics, Apr. 28, 2008, pp. 2124-2136, vol. 35, No. 5, American Association of Physicists in Medicine.

S Ouadah et al., "Self-calibration of cone-beam CT geometry using 3D-2D image registration", Phys Med Biol., Apr. 7, 2016, pp. 2613-2632, vol. 61, No. 7.

* cited by examiner

COMPUTED TOMOGRAPHY DEVICE AND COMPUTED TOMOGRAPHY IMAGE CORRECTION METHOD USING THE SAME

CROSS-REFERENCE TO RELATED APPLICATIONS

This U.S. non-provisional patent application claims priority under 35 U.S.C. § 119 of Korean Patent Application No. 10-2017-0003061, filed on Jan. 9, 2017, the entire contents of which are hereby incorporated by reference.

BACKGROUND

The present disclosure herein relates to a three-dimensional image processing, and more particularly, to a computed tomography device and a computed tomography image correction method using the same.

An X-ray image capturing device is useful for diagnosing diseases and examining health because it is able to photograph the inside without dissecting a human body. Particularly, a computed tomography device receives attention in that the inside of a human body is viewed in three dimensions by imaging the human body as a single layer.

A computed tomography device extracts a plurality of two-dimensional images while an X-ray light source rotates around a subject, and reconstructs a three-dimensional image using the plurality of two-dimensional images. The three-dimensional image may be reconstructed with high accuracy by knowing precisely the position of a light source and the coordinates of a subject at the time of extracting the two-dimensional image. Conventionally, a computed tomography device fixed in a room and having a large size is provided to ensure the accuracy of a three-dimensional image.

In recent years, a compact computed tomography device capable of securing low cost, movable possibility, and patient convenience receives attention. In such a computed tomography device, the movement of a gantry for supporting a light source may become unstable as compared with the above-mentioned large computed tomography device. Therefore, there is a demand for a method for ensuring the stability of the movement of the gantry and ensuring the accuracy of a reconstructed three-dimensional image.

SUMMARY

The present disclosure provides a computed tomography device, which provides a stable three-dimensional reconstruction image despite the unstable movement trajectory of the gantry and the involuntary movement of the patient, and a computed tomography image correction method using the same.

An embodiment of the inventive concept provides a computed tomography device including a gantry, a detector, and an arm. The light source irradiates light, a detector is disposed facing the light source and for receiving the light. The arm supports the light source and the detector. The gantry photographs a subject where a marker is disposed to generate a two-dimensional detection image. The two-dimensional detection image includes a plurality of markers.

In an embodiment, an image processing processor may receive a two-dimensional detection image for a subject from the detector to convert the received two-dimensional detection image to two-dimensional detection image data, and generate three-dimensional reconstruction image data from the two-dimensional detection image data.

In an embodiment, the image processing processor may generate an initial transformation projection matrix for mapping coordinates of the subject according to a movement path of the gantry to two-dimensional coordinates. The image processing processor may generate three-dimensional reference data by performing a back projection operation on the two-dimensional detection image data. The image processing processor may generate two-dimensional reference data based on the three-dimensional reference data and the initial transformation projection matrix. The image processing processor may generate a corrected transformation projection matrix based on a difference between the two-dimensional reference data and the two-dimensional detection image data. The image processing processor may generate the three-dimensional reconstruction image data based on the corrected transformation projection matrix.

In an embodiment, the image processing processor may operate in one of a rigid body transformation mode and a non-rigid body transformation mode. In the rigid body transformation mode, the corrected transformation projection matrix may be generated so that correction amounts of target images corresponding to the plurality of markers are equal to each other. In the non-rigid body transformation mode, the corrected transformation projection matrix may be generated so that correction amounts of target images corresponding to a part of the plurality of markers are different from correction amounts of target images corresponding to the rest of the plurality of markers.

In an embodiment of the inventive concept, a computed tomography image correction method includes: initializing a transformation projection matrix, generating two-dimensional detection image data, generating two-dimensional reference data, correcting the transformation projection matrix, and generating a three-dimensional reconstruction image.

In an embodiment, in the generating of the two-dimensional detection image data, the gantry may photograph a subject and the two-dimensional detection image data may include target data.

In an embodiment, the generating of the two-dimensional reference data may include detecting the target data from the two-dimensional detection image data; generating the three-dimensional reference data from the target data, and calculating the three-dimensional reference data and the initialized transformation projection matrix. In the correcting of the transformation projection matrix, the corrected transformation projection matrix may be generated based on a difference between the two-dimensional reference data and the target data.

BRIEF DESCRIPTION OF THE FIGURES

The accompanying drawings are included to provide a further understanding of the inventive concept, and are incorporated in and constitute a part of this specification. The drawings illustrate exemplary embodiments of the inventive concept and, together with the description, serve to explain principles of the inventive concept. In the drawings.

DETAILED DESCRIPTION

In the following, embodiments of the inventive concept will be described in detail so that those skilled in the art easily carry out the inventive concept.

Figure 1:
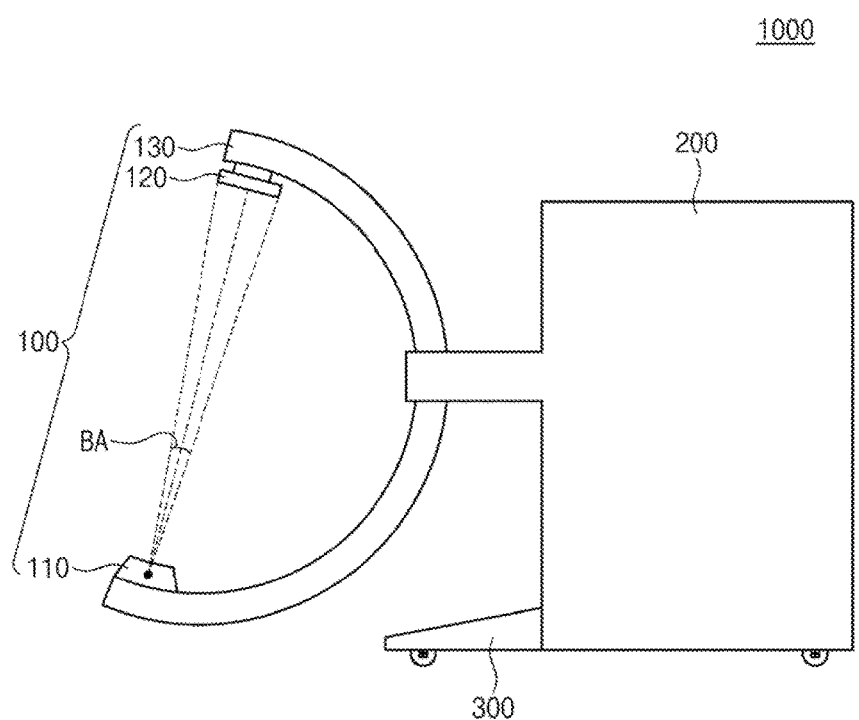
FIG. 1 is a sectional view of a computed tomography device according to an embodiment of the inventive concept.

FIG. 1 is a sectional view of a computed tomography device according to an embodiment of the inventive concept.

Referring to FIG. 1, a compute tomography device 1000 includes a gantry 100, a body portion 200, and a moving portion 300. The gantry 100 includes a light source 110, a detector 120, and an arm 130.

The light source 110 irradiates light to a subject. The light source 110 may irradiate an X-ray capable of traversing a subject toward a subject. The light source 110 provides light having a constant light angle BA to a subject. The size of the light angle BA is not limited, but the light angle BA may be provided so that light is irradiated to the entire range of the subject to be photographed. That is, while the light source 110 moves around a subject, the width of the subject may change in a direction perpendicular to the direction of light irradiation, and even with such a changing width of the subject, the light angle BA may have an angle at which the capturing range of the subject is secured in all moving paths of the light source 110.

The detector 120 is disposed to face the subject with the light source 110 interposed therebetween. The detector 120 receives the light emitted from the light source 110. The detector 120 has a width to accommodate light having the light angle BA. Since the light provided by the light source 110 travels with the light angle BA, the incident area of the light increases as the distance from the light source 110 increases. Thus, the width of the detector 120 is formed to be larger than the width of the subject defined on the cross section parallel to the detector 120. The detector 120 may form a receiving surface to have the light irradiation direction of the light source 110 as a vertical axis. That is, it is difficult to generate an accurate three-dimensional reconstruction image if the direction in which the detector 120 receives light is changed while the light source 110 and the detector 120 moves around the subject. The detector 120 provides a two-dimensional detection image projected from a subject to an image processing processor described later.

The arm 130 supports the light source 110 and the detector 120. The light source 110 is disposed at one side of the arm 130 and the detector 120 is disposed at the other side of the arm 130. The arm 130 may have a C-shape. That is, the arm 130 provides an opening for allowing a subject is placed between the light source 110 and the detector 120. The arm 130 moves around the subject. As the arm 130 moves, the light source 110 and the detector 120 also move around the subject. For example, the trace of the arm 130 may be circular. In addition, the distance between the light source 110 and the detector 120 may correspond to the diameter of the circular movement trace of the arm 130. The arm 130 provides a firm support so that the distance between the light source 110 and the detector 120 is constant and the angle of the light irradiated to the detector 120 is not changed. Thus, the arm 130 allows the light source 110 to photograph the subject at various angles.

Even if the gantry 100 performs repetitive capturing, it should rotate along the same trace so that the three-dimensional reconstruction image is not distorted. That is, as the gantry 100 rotates, the detector 120 sequentially receives the light that the light source 110 provides to the subject, and provides a plurality of two-dimensional detection images for a subject to the image processing processor. Then, the coordinates of the plurality of two-dimensional detection images are combined to generate a three-dimensional reconstruction image. The stability of a trace as the gantry 100 performs repetitive capturing is determined by the rigid coupling between the body 200 and the gantry 100 and the rigid coupling between the arm 130 and the light source 110 and between the arm 130 and the detector 120. However, the trace of the gantry 100 may not be constant in the compact and mobile computed tomography device 1000. A stable three-dimensional reconstruction image generation process in such the computed tomography device 1000 will be described later.

The body portion 200 supports the gantry 100. The body portion 200 accommodates an image processing processor that controls the movement of the gantry 100, receives a two-dimensional detection image from the detector 120, and performs image processing. In addition, the body portion 200 accommodates various control units or driving devices for computer tomography Details will be described later.

The moving portion 300 is configured to allow the computed tomography device 1000 to move easily. For example, the moving portion 300 is connected to the lower part of the body portion 200 and may include a wheel. The moving unit 300 may easily move to a subject and include another fixing means for preventing the computed tomography device 1000 from moving when the subject is photographed. The computed tomography device 1000 according to an embodiment of the inventive concept may secure accessibility to a patient, and achieve miniaturization and economical efficiency.

Figure 2:
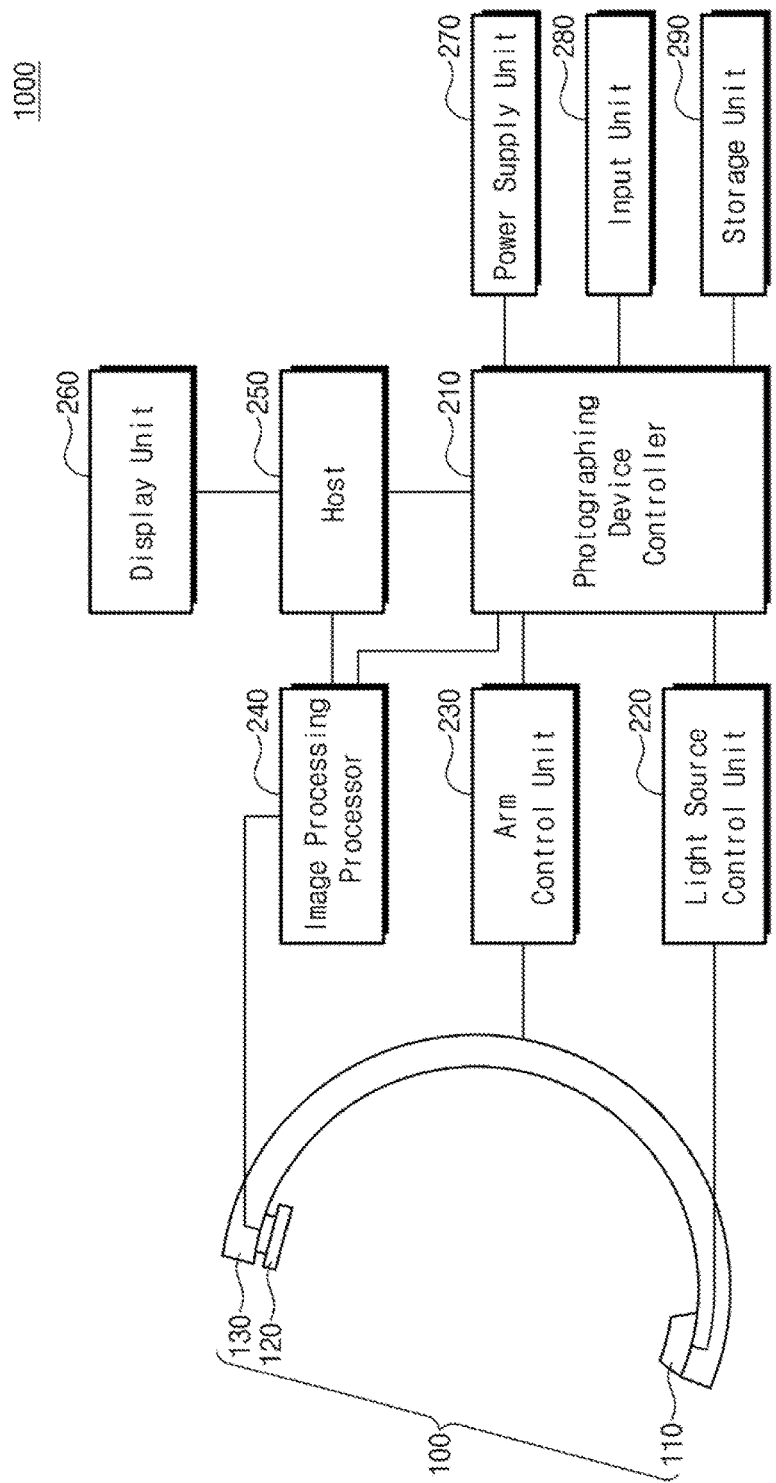
FIG. 2 is a block diagram of a computed tomography device according to an embodiment of the inventive concept.

FIG. 2 is a block diagram of a computed tomography device according to an embodiment of the inventive concept.

Referring to FIG. 2, the computed tomography device 1000 includes a gantry 100, a photographing device controller 210, a light source control unit 220, an arm control unit 230, an image processing processor 240, a host 250, a display unit 260, a power supply unit 270, an input unit 280, and a storage unit 290. The gantry 100 includes a light source 110, a detector 120, and an arm 130, and has substantially the same configuration as the gantry 100 of FIG. 1 and performs the same function, so a detailed description will be omitted.

The photographing device controller 210, the light source control unit 220, the arm control unit 230, the image processing processor 240, the power supply unit 270, the input unit 280, and the storage unit 290 may be received in the body portion 200 of FIG. 1. However, the inventive concept is not limited thereto, and the components may be provided to other components, for example, separate components connected to the gantry 100 or the body portion 200. For example, the light source control unit 220 may be included in the light source 110. The host 250 and the display unit 260 may be integrally formed with the body 200, but are not limited thereto and may be provided as separate components to form a computed tomography system.

The photographing device controller 210 performs the overall control function of the computed tomography device 1000. The photographing device controller 210 applies control signals to the light source control unit 220, the arm control unit 230, and the image processing processor 240. The photographing device controller 210 may receive three-dimensional reconstruction image data from the image processing processor 240 and then, may provide it to the host 250 or may store it in the storage unit 290. For example, the photographing device controller 210 may control a light irradiation time by providing a trigger signal or a clock signal to the light source control unit 220, and may provide a trigger signal or a clock signal to the arm control unit 230 to control the rotation speed and rotation range of the arm 130. That is, in order to photograph a subject stably, the photographing device controller 210 may control the light source 110 to stably provide light during the movement of the arm 130 so that a two-dimensional detection image is obtained.

The light source control unit 220 is electrically connected to the light source 110. The light source control unit 220 receives a control signal from the photographing device controller 210 and controls the light source 110. The light source control unit 220 may control the light irradiation time of the light source 110. The light source control unit 220 may control the number of light irradiation times as many as the number of two-dimensional detection images required during the movement of the arm 130. In addition, the light source control unit 220 may adjust the light angle BA of the light irradiated by the light source 110 in consideration of the area of a subject, and when light is irradiated to a human body, adjust the amount of light in consideration of a harmless range to the human body and the stability of an image.

The arm control unit 230 receives a control signal from the photographing device controller 210 and controls the arm 130. The arm control unit 230 may control the movement range or movement speed of the arm 130. The arm control unit 230 may control a motor connected to the arm 130 to move the arm 130.

The image processing processor 240 is electrically connected to the detector 120. The image processing processor 240 may receive a control signal from the photographing device controller 210 and generate a three-dimensional reconstruction image based on a two-dimensional detection image received from the detector 120. The image processing processor 240 may receive a plurality of two-dimensional detection images by the light periodically irradiated by the light source 110 during the movement of the arm 130. The image processing processor 240 extracts the coordinates of the plurality of two-dimensional detection images, calculates the positional relationship between the two-dimensional detection images, and generates a three-dimensional reconstruction image. Details will be described later.

The host 250 may communicate with the imaging device controller 210 via a host interface or exchange data with the image processing processor 240. For example, the host 250 may be configured as a host personal computer (PC). The host interface may include a protocol for performing data exchange between the photographing device controller 210 or the image processing processor 240 and the host 250.

The display unit 260 may receive image data from the host 250 and generate a data voltage based on the image data to display an image. The display unit 260 may display an image on the three-dimensional reconstruction image generated by the image processing processor 240. Also, the display unit 260 may receive and display the two-dimensional detection image. For example, the display unit 260 may include a Liquid Crystal Display (LCD), an Organic Light Emitting Diode (OLED), an Active Matrix OGLED (AMOLED), a flexible display, or an electronic ink.

The power supply unit 270 supplies a power supply voltage to the photographing device controller 210. The photographing device controller 210 may receive the power supply voltage from the power supply unit 270 to control the light source control unit 220, the arm control unit 230, and the image processing processor 240 or communicate with the host 250.

The input unit 280 is configured to receive driving signals for operating the computed tomography device 1000 from an operator of the computed tomography device 1000. For example, the input unit 280 may receive light amount, light angle, photographing period, and the like from an operator. Unlike FIG. 2, the input unit 280 may be connected to the host 250, and in this case, a driving signal may be delivered to the photographing device controller 210 via the host 250.

The storage unit 290 may store data generated by the computed tomography device 1000. For example, the storage unit 290 may store three-dimensional reconstruction image data, two-dimensional detection data, and the like generated from the image processing processor 240. The storage unit 290 may be used as a main storage unit or an auxiliary storage unit for the computed tomography device 1000.

Figure 3:
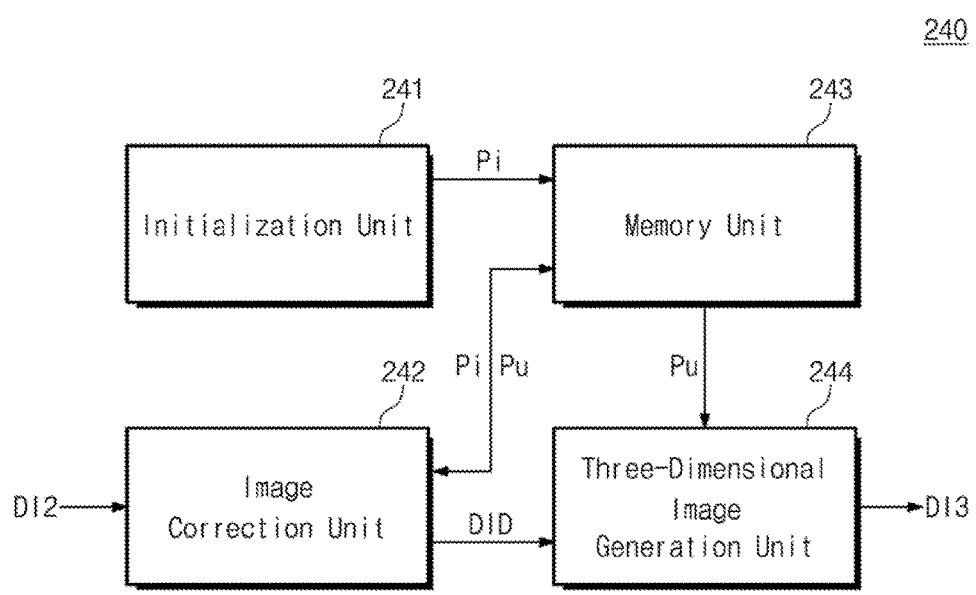
FIG. 3 is a block diagram of an image processing processor of FIG. 2.

FIG. 3 is a block diagram of the image processing processor 240 of FIG. 2.

Referring to FIG. 3, the image processing processor 240 may include an initialization unit 241, an image correction unit 242, a memory unit 243, and a three-dimensional image generation unit 244.

The initialization unit 241 generates an initial transformation projection matrix Pi. The transformation projection matrix means a matrix for mapping coordinates of a three-dimensional subject to two-dimensional coordinates. The initial transformation projection matrix Pi means an initial value of the transformation projection matrix that does not undergone the image correction process in order to generate the 3D reconstruction image data DI3. The initialization unit 241 may provide the initial transformation projection matrix Pi to the memory unit 243.

The initialization unit 241 may generate the initial transformation projection matrix Pi in various ways. As one example, the initial transformation projection matrix Pi may be generated assuming that the gantry 100 moves along an ideal trace. When it is assumed that the gantry 100 travels along an ideal circular trace, the distance between the light source 110 and the detector 120 is constant and the detector 120 receives the same amount of light by the specified light angle. That is, the theoretical coordinates for a two-dimensional detection image according to the position of a subject may be calculated, and an initial transformation projection matrix for a case where the subject is photographed in the ideal circular trace based on the theoretical value of the movement trace of the arm 130 may be calculated. In this case, the initialization unit 241 may generate the initial transformation projection matrix Pi based on the theoretical value, without receiving any additional data from the gantry 100.

As another example, the initialization unit 241 may generate the initial transformation projection matrix Pi using a correction phantom that accurately knows the three-dimensional coordinates. In relation to the correction phantom, a plurality of markers that know the three-dimensional coordinates may be formed. The plurality of markers may be formed so that no more than three markers are disposed on an arbitrary line passing through the correction phantom. The shape of the correction phantom is not limited and may have various shapes. The gantry 100 may generate a plurality of two-dimensional detection images by photographing a correction phantom, and may combine a plurality of marker images formed in the two-dimensional detection image to generate the initial transformation projection matrix Pi. In this case, the initialization unit 241 may receive the two-dimensional detection image of the correction phantom from the gantry 100.

The initial transformation projection matrix Pi is described as defining the relationship between the coordinates of the three-dimensional subject and the two-dimensional coordinates, but is not limited thereto. For example, the initial transformation projection matrix Pi may include parameters for defining a geometric structure as the gantry 100 rotates or moves.

The image correction unit 242 receives a two-dimensional detection image DI2 from the detector 120. The two-dimensional detection image DI2 corresponds to an image formed as the light irradiated from the light source 110 travels a subject and arrives at the detector 120. The two-dimensional detection image DI2 is provided in plurality according to the movement of the gantry 100 and the sequential light irradiation of the light source 110. The image correction unit 242 corrects the matrix value of the initial transformation projection matrix Pi based on the two-dimensional detection image DI2. The image correction unit 242 generates a corrected transformation projection matrix Pu based on the two-dimensional detection image DI2. The image correction unit 242 may provide the corrected transformation projection matrix Pu to the memory unit 243. In addition, the image correction unit 242 modulates the two-dimensional detection image DI2 to generate two-dimensional detection image data DID. The image correction unit 242 provides the two-dimensional detection image data DID to the three-dimensional image generation unit 244.

The image correction unit 242 performs a back projection operation on the two-dimensional detection image data DID to generate three-dimensional reference data r3, and generates two-dimensional reference data r2 based on the three-dimensional reference data r3 and the initial transformation projection matrix Pi. The image correction unit 242 generates a corrected transformation projection matrix Pu based on the difference between the two-dimensional reference data r2 and the two-dimensional detection image data DID. The specific process of generating the corrected transformation projection matrix Pu will be described later.

The memory unit 243 receives the initial transformation projection matrix Pi from the initialization unit 241 and receives the corrected transformation projection matrix Pu from the image correction unit 242. The memory unit 243 may provide the initial transformation projection matrix Pi to the image correction unit 242. The memory unit 243 may provide the corrected transformation projection matrix Pu to the three-dimensional image generation unit 244. However, the inventive concept is not limited thereto, and the memory unit 243 may store various data for image processing. For example, the memory unit 243 may store two-dimensional detection image data DID and three-dimensional reconstruction image data DI3.

The memory unit 243 may include at least one of non-volatile memory devices such as Read Only Memory (ROM), Programmable ROM (PROM), Electrically Programmable ROM (EPROM), Electrically Erasable and Programmable ROM (EEPROM), a flash memory device, Phase-change RAM (PRAM), Magnetic RAM (MRAM), Resistive RAM (RRAM), or Ferroelectric RAM (FRAM) or may include at least one of volatile memory devices such as Static RAM (SRAM), Dynamic RAM (DRAM) or Synchronous DRAM (SDRAM). Unlike FIG. 3, the image processing processor 240 may store data such as the initial transformation projection matrix Pi or the corrected transformation projection matrix Pu in the storage unit 290 of FIG. 2, and request the storage unit 290 to receive data.

The three-dimensional image generation unit 244 receives the two-dimensional detection image data DID from the image correction unit 242. The three-dimensional image generation unit 244 receives the corrected transformation projection matrix Pu from the memory unit 243. Alternatively, the three-dimensional image generation unit 244 may receive the corrected transformation projection matrix Pu directly from the image correction unit 242. The three-dimensional image generation unit 244 reconstructs the two-dimensional detection image data DID into the three-dimensional reconstruction image data DI3 using the corrected transformation projection matrix Pu. For example, the three-dimensional image generation unit 244 inversely transforms the corrected transformation projection matrix Pu and back-projects the two-dimensional detection image data DID using the inversely-transformed corrected transformation projection matrix Pu to generate the three-dimensional reconstruction image data DI3.

Figure 4:
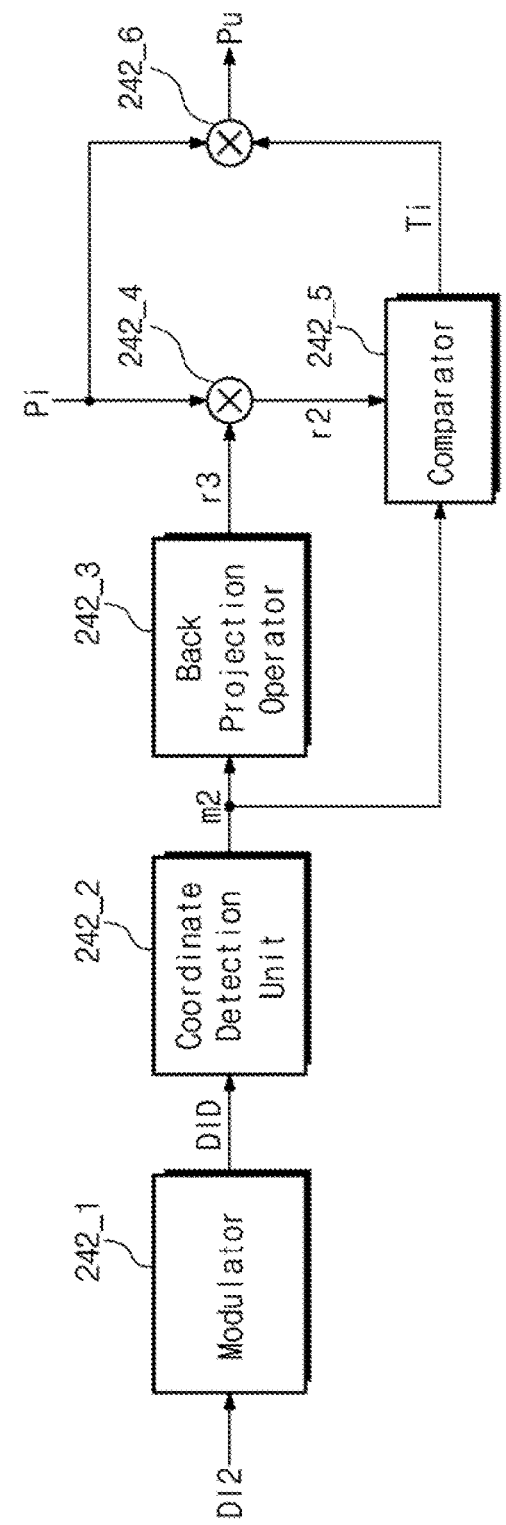
FIG. 4 is a block diagram of an image correction unit of FIG. 3.

FIG. 4 is a block diagram of the image correction unit 242 of FIG. 3.

Referring to FIG. 4, the image correction unit 242 includes a modulator 242_1, a coordinate detection unit 242_2, a back projection operator 242_3, a first multiplication operator 242_4, a comparator 242_5, and a second multiplication operator 242_6.

The modulator 242_1 receives the two-dimensional detection image DI2 from the gantry 100. The modulator 242_1 converts the two-dimensional detection image DI2 into two-dimensional detection image data DID. The modulator 242_1 may include an A/D converter for converting an analog image to digital data.

The coordinate detection unit 242_2 detects target data m2 from the two-dimensional detection image data DID. The target data m2 is data corresponding to the target image in the two-dimensional detection image DI2 on which a subject is projected. The target data m2 may include two-dimensional coordinate information of the target image. The target image may be an image by a subject or a marker attached on a table that supports the subject. A plurality of markers may be provided and attached to the subject or table. The marker may include a radiopaque material. Accordingly, the gantry 100 may be photographed to identify the coordinates of the target image by the marker. The target image is not limited to an image corresponding to the marker. For example, the target image may specify high density objects such as a corner of a protruding bone and may be defined as an image corresponding thereto.

The coordinate detection unit 242_2 may extract data having a specific value from the two-dimensional detection image data DID to detect the target data m2. That is, the coordinate detection unit 242_2 may detect the target data m2 by using a data value difference of an impermeability-reflected target image of a marker. However, the inventive concept is not limited thereto, and the coordinate detection unit 242_2 may detect the target data m2 based on a data value change amount with adjacent data. Although it is shown that the coordinate detection unit 242_2 detects the coordinates of the marker in a digital manner, the inventive concept is not limited thereto. For example, the coordinate detection unit 242_2 may receive the two-dimensional detection image DI2 to detect the target image coordinates, and then the modulator 242_1 may convert the target image to the target data m2. A specific explanation for generating the two-dimensional detection image DI2 such as the arrangement of the marker and the photographing of the gantry 100 will be described later with reference to FIG. 5.

The back projection operator 242_3 receives the target data m2 and generates the three-dimensional reference data r3 based on the target data m2. That is, the back projection operator 242_3 performs a back projection operation in the direction of the light source 110 to which light is irradiated in order to convert the target data m2 corresponding to the two-dimensional coordinates into the three-dimensional coordinates. Also, the three-dimensional reference data r3 is generated by correcting the error of the three-dimensional coordinate due to the instability of the movement path of the gantry 100. The process of generating the specific three-dimensional reference data r3 will be described later with reference to FIGS. 6 and 7.

The first multiplication operator 242_4 receives the three-dimensional reference data r3 from the back projection operator 242_3 and receives the initial transformation projection matrix Pi from the memory unit 243. Alternatively, the first multiplication operator 242_4 may receive the initial transformation projection matrix Pi directly from the initialization unit 241. The first multiplication operator 242_4 generates a two-dimensional reference data r2 by performing matrix multiplication of the initial transformation projection matrix Pi and the three-dimensional reference data r3 as shown in Equation 1.

$$r2_j = Pi \cdot r3_j \quad \text{[Equation 1]}$$

Referring to Equation 1, when j markers are attached to a subject, two-dimensional reference data r2 corresponding to j markers is generated. For example, when four markers are attached to a subject, the first multiplication operator 242_4 multiplies the three-dimensional reference data r3 corresponding to the first to fourth markers by the first transformation projection matrix Pi to generate the two-dimensional reference data r2 corresponding to the first to fourth markers. That is, the first multiplication operator 242_4 generates the two-dimensional reference data r2 including the two-dimensional coordinate information by mapping the three-dimensional reference data r3 including the three-dimensional coordinate information of the marker into two-dimensional coordinates.

The comparator 242_5 receives the two-dimensional reference data r2 from the first multiplication operator 242_4. The comparator 242_5 receives the target data m2 from the coordinate detection unit 242_2. The comparator 242_5 compares the two-dimensional reference data r2 and the target data m2 to calculate a transformation matrix Ti. Specifically, the comparator 242_5 calculates the distance between the coordinate information included in the two-dimensional reference data r2 and the coordinate information included in the two-dimensional target data m2. When the comparator 242_5 shifts (e.g., tx, ty, tz) the target data m2 corresponding to each marker j to the X axis, the Y axis, or the Z axis defining the three-dimensional space and/or rotates (e.g., ax, ay, az) by using the X axis, the Y axis, or the Z axis as a rotation axis, a cost function is calculated as shown in Equation 2 to minimize the distance between the two-dimensional reference data r2 corresponding to each marker j.

$$\operatorname*{argmin}_{\substack{tx, ty, tz \\ ax, ay, az}} \sum_{marker\ j} |r2_j - m2_j|^2 \quad \text{[Equation 2]}$$

The transformation matrix Ti is calculated on the basis of the parameters for minimizing the cost function such as Equation 2. That is, the calculated transformation matrix Ti value is determined by the shaking of the gantry 100 or the movement of the subject. In an ideal environment without the shaking of the gantry 100 or the movement of the subject, the target data m2 and the two-dimensional reference data r2 are the same.

The second multiplication operator 242_6 receives the transformation matrix Ti from the comparator 242_5 and receives the initial transformation projection matrix Pi from the memory unit 243. Alternatively, the second multiplication operator 242_6 may receive the initial transformation projection matrix Pi directly from the initialization unit 241. The second multiplication operator 242_6 generates the corrected transformation projection matrix Pu by performing a matrix multiplication operation on the initial transformation projection matrix Pi and the transformation matrix Ti as shown in Equation 3.

$$Pu = Pi \cdot Ti \text{ or } Ti \cdot Pi \quad \text{[Equation 3]}$$

The second multiplication operator 242_6 provides the corrected transformation projection matrix Pu to the memory unit 243. The memory unit 243 stores the corrected transformation projection matrix Pu. Alternatively, the second multiplication operator 242_6 may provide the corrected transformation projection matrix Pu to the three-dimensional image generation unit 244 to generate the three-dimensional reconstruction image data DI3.

Figure 5:
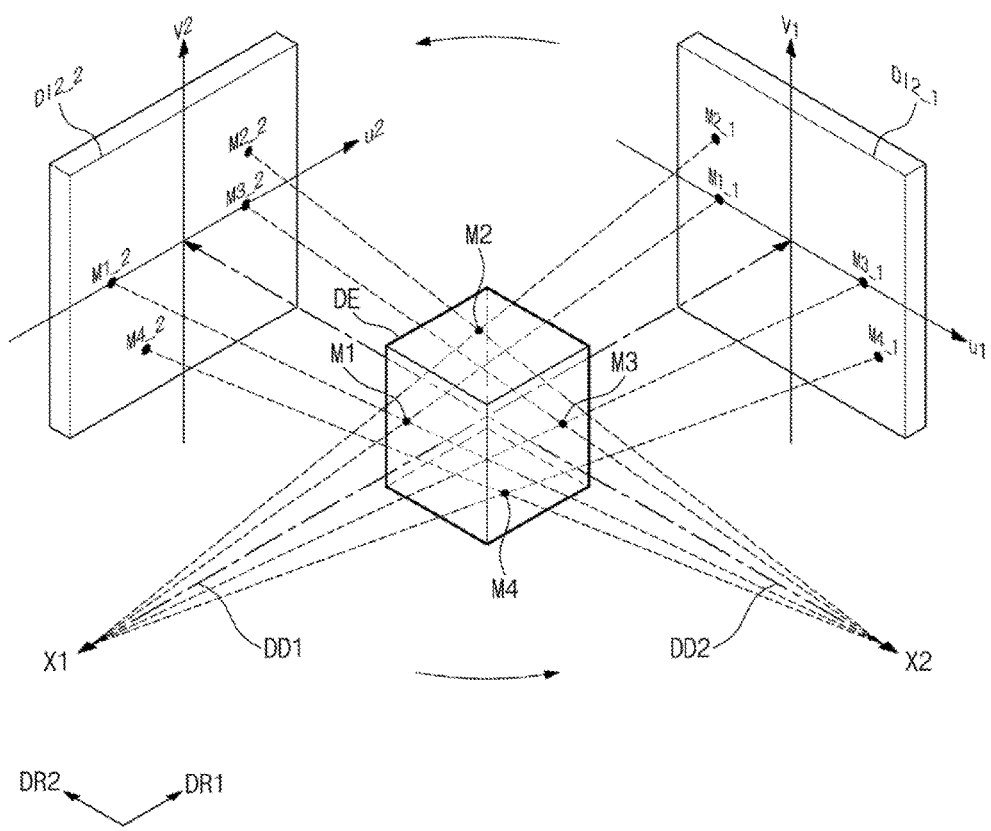
FIG. 5 is a view illustrating a process of generating a two-dimensional detection image and implementing a three-dimensional coordinate.

FIG. 5 is a view illustrating a process of generating a two-dimensional detection image and implementing a three-dimensional coordinate using the same.

Referring to FIG. 5, first to fourth markers M1 to M4 are attached to a subject DE. However, the number of markers is not limited thereto. As the number of markers used increases, an accuracy of the transformation matrix Ti corresponding to the two-dimensional detection image DI2 increases. The first to fourth markers M1 to M4 are attached to the subject DE so that no more than three markers are placed on an arbitrary line projecting the subject DE. More preferably, the first to fourth markers M1 to M4 are attached to the subject DE so that no more than two markers are arranged in the direction in which the light is irradiated. This is to prevent the overlapping of the target images corresponding to the first to fourth markers M1 to M4 in the two-dimensional detection image DI2 of the photographed subject. Although FIG. 5 illustrates the subject DE as a hexahedron for convenience of explanation, the subject DE may be understood as a part of a human body or the like for generating the two-dimensional detection image DI2.

The two-dimensional detection image DI2 includes a first two-dimensional detection image DI2_1 and a second two-dimensional detection image DI2_2. The first two-dimensional detection image DI2_1 is an image generated as a light source irradiates a first light X1 at the first time point and the first light X1 reaches a detector. The first light X1 is irradiated to have a light angle, thereby reaching all of the first to fourth markers M1 to M4 in the first direction DR1. The first two-dimensional detection image DI2_1 includes four first target images M1_1 to M1_4 corresponding to the first to fourth markers M1 to M4.

The second two-dimensional detection image DI2_2 is generated at the second time point after a predetermined time elapses from the first time point. The gantry 100 rotates around the subject DE between the first and second time points. At the second time point, the second two-dimensional detection image DI2_2 is an image generated as the second light X2 reaches a detector. The second light X2 is irradiated to have the same light angle as the first light X1 in the second direction DR2 that intersects the first direction DR1. The second two-dimensional detection image DI2_2 includes four second target images M2_1 to M2_4 corresponding to the first to fourth markers M1 to M4. Although FIG. 5 exemplarily illustrates the two-dimensional detection image DI2 according to the first and second time points, a large number of two-dimensional detection images are generated according to the movement path of the gantry 100.

The three-dimensional coordinates of the first to fourth markers M1 to M4 attached to the subject DE may be extracted using the first two-dimensional detected image DI2_1 and the second two-dimensional detected image DI2_2. The first light X1 is irradiated in the first direction DR1 toward the center point of a detector. The distance between the light source and the detector may correspond to the first distance DD1, which is the path along which the first light X1 travels to the center of the detector. The three-dimensional coordinate away from the center of the detector by the first distance DD1 in the first direction DR1 is defined as a first light source point. In this case, virtual restoration lines extending from the four first target images M1_1 to M1_4 to the first light source point may be specified.

In the same manner, a second light X2 is irradiated in the second direction DR2 from the second light source point toward the center point of the detector. The distance between the light source and the detector may correspond to the second distance DD2. In this case, virtual restoration lines extending from the four second target images M2_1 to M2_4 to the second light source point may be specified. The intersection points of the restoration lines extending to the first light source point and the restoration lines extending to the second light source point may correspond to the three-dimensional coordinates of the first to fourth markers M1 to M4.

Therefore, when the distance between the light source and the detector and the movement paths of the light source and the detector are accurately specified, the three-dimensional coordinates of the first to fourth markers M1 to M4 may be calculated by the back projection computation. However, when the movement trace of the gantry 100 is unstable, the first distance DD1 and the second distance DD2 corresponding to the distance between the light source and the detector may be different, and thus the accuracy of the restoration lines decreases. Also, since errors occur in the movement path of the gantry 100, the accuracy of the restoration lines extending from the first two-dimensional detection image DI2_1 and the second two-dimensional detection image DI2_2 decreases.

Figure 6:
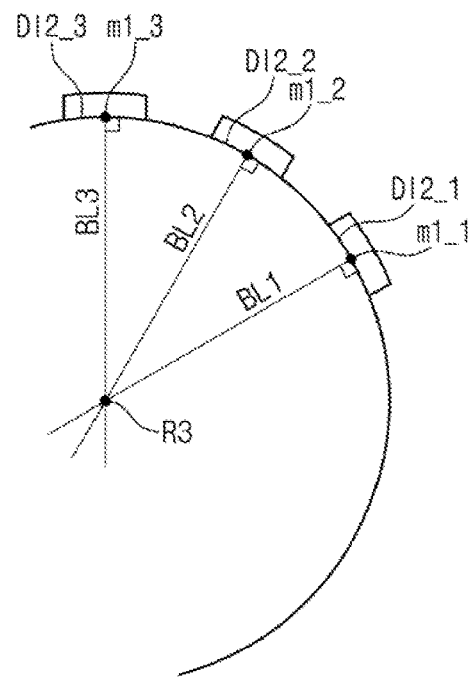
FIGS. 6 and 7 are views illustrating the calculation of three-dimensional reference data.
Figure 7:
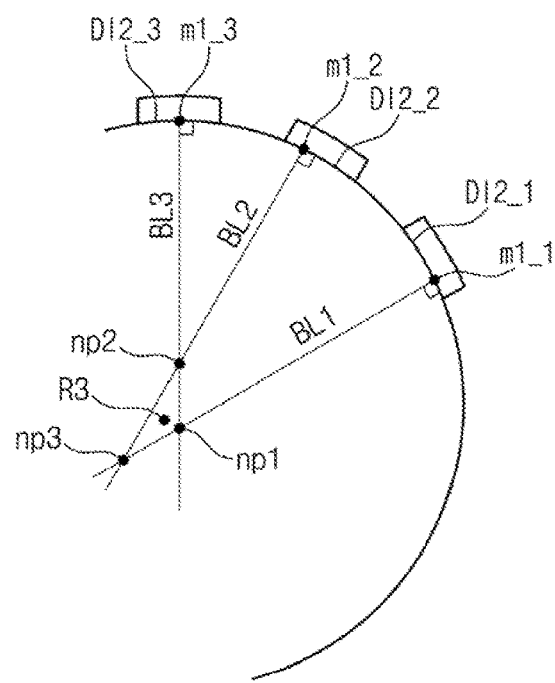

FIGS. 6 and 7 are views illustrating the generation of three-dimensional reference data when an error occurs in the movement path of a gantry. FIG. 6 is a view illustrating the calculation of three-dimensional reference data according to an ideal movement path of a gantry. FIG. 7 is a view illustrating the calculation of three-dimensional reference data according to a non-ideal movement path of a gantry. The non-ideal movement path of the gantry as shown in FIG. 7 may occur due to the deflection of the gantry 100 and the performance degradation of the motor controlling the movement of the gantry.

Referring to FIG. 6, while rotating counterclockwise according to the passage of time, a detector generates a first two-dimensional detection image DI2_1, a second two-dimensional detection image DI2_2, and a third two-dimensional detection image DI2_3. The first to third two-dimensional detection images DI2_1 to DI2_3 include first to third target images m1_1 to m1_3 corresponding to the markers formed on the subject. For convenience of explanation, it is assumed that the gantry has a circular movement path, and a point at which the marker is formed is the center point of the circular movement path of the gantry.

An imaginary restoration line extending in a direction perpendicular to the detector at the time of obtaining the first two-dimensional detection image DI2_1 and contacting the first target image m1_1 is defined as a first restoration line BL1. An imaginary restoration line extending in a direction perpendicular to the detector at the time of obtaining the second two-dimensional detection image DI2_2 and contacting the second target image m1_2 is defined as a second restoration line BL2. An imaginary restoration line extending in a direction perpendicular to the detector at the time of obtaining the third two-dimensional detection image DI2_3 and contacting the third target image m1_3 is defined as a third restoration line BL3. This is because the point at which the marker is formed is the center point of the circular movement path of the gantry. In principle, the extending directions of the first to third restoration lines BL1 to BL3 correspond to the direction from the first to third target images m1_1 to m1_3 toward the center of the light source.

When the gantry has an ideal movement path, the first to third restoration lines BL1 to BL3 have one intersection point. This is because the direction in which the light travels to the marker is the same as the extending directions of the first to third restoration lines BL1 to BL3. The intersection point of the first to third restoration lines BL1 to BL3 is defined as a three-dimensional reference point R3. The three-dimensional reference data r3 includes coordinate information of the three-dimensional reference point R3. That is, when the gantry has an ideal movement path, the three-dimensional reference point R3 may be specified by a simple back projection operation, and the three-dimensional reference data r3 may be calculated.

Referring to FIG. 7, while rotating counterclockwise according to the passage of time, a detector generates a first two-dimensional detection image DI2_1, a second two-dimensional detection image DI2_2, and a third two-dimensional detection image DI2_3. The first to third two-dimensional detection images DI2_1 to DI2_3 include first to third target images m1_1 to m1_3 corresponding to the markers formed on the subject. As shown in FIG. 6, it is assumed that the marker of FIG. 7 is formed at the center point of the circular movement path of the gantry.

Under the same conditions as in FIG. 6, in FIG. 7, the first to third restoration lines BL1 to BL3 contacting the first to third target images m1_1 to m1_3 and extending in a direction perpendicular to the detector are defined. However, unlike FIG. 6, the first to third restoration lines BL1 to BL3 of FIG. 7 do not have one intersection point. The first restoration line BL1 and the third restoration line BL3 have a first intersection point np1. The second restoration line BL2 and the third restoration line BL3 have a second intersection point np2. The first restoration line BL1 and the second restoration line BL2 have a third intersection point np3. The reason that a plurality of intersection points are generated is that the direction in which the light travels to the marker differs from the extending direction of at least one of the first to third restoration lines BL1 to BL3. That is, the gantry may not move and may wobble while drawing an ideal trace and deflection may occur by gravity.

When the gantry has a non-ideal movement path, the average value of the three-dimensional coordinates of each of the first to third intersection points np1 to np3 may be specified as the three-dimensional reference point R3. The three-dimensional reference data r3 includes coordinate information of the three-dimensional reference point R3. In other words, the back projection operator 242_3 of FIG. 4 performs a back projection operation on the target data including the coordinate information of the first to third target images m1_1 to m1_3 to extract a plurality of intersection point coordinates, and calculates the average value of the plurality of intersection point coordinates to calculate the three-dimensional reference data r3. However, the three-dimensional reference point R3 is not limited thereto, and may be specified in various ways. For example, the three-dimensional reference point R3 may be calculated by calculating a cost function that minimizes the distance from the first to third restoration lines BL1 to BL3. Also, the three-dimensional reference point R3 may be selected as one intersection point where the largest number of restoration lines contact among the plurality of restoration lines. The restoration lines for generating the three-dimensional reference point R3 may be determined through a back projection operation using the initial transformation projection matrix Pi. That is, a line extending vertically from the two-dimensional detection image may be defined as a restoration line as shown in FIGS. 6 and 7. However, in order to ensure the accuracy of the three-dimensional reference point R3, a restoration line may be defined through a back projection operation based on the initial transformation projection matrix Pi.

FIG. 7 is limited to a case where an error of the movement trace occurs in a plane perpendicular to the rotation axis of the gantry. For example, when the swing of the gantry occurs in the direction of the rotation axis of the gantry, the first to third restoration lines BL1 to BL3 may be in a twisted position having no intersection point. In this case, the first to third restoration lines BL1 to BL3 may be orthogonally projected on the same plane in order not to consider a moving component in the direction of the rotation axis of the gantry, thereby generating a plurality of intersection points on the two-dimensional plane. Then, the three-dimensional coordinates of the first to third restoration lines BL1 to BL3 corresponding to the intersection points may be extracted and an average value may be calculated to specify the three-dimensional reference point R3.

For convenience of description, although FIGS. 6 and 7 illustrate that the first to third two-dimensional detection images DI2_1 to DI2_3 are generated, three or more two-dimensional detection images may be generated in order to generate three-dimensional reference data. As the number of the two-dimensional detection images used increases, an accuracy of the three-dimensional reference point R3 corresponding to the marker increases, so that an error between the actual marker position and the three-dimensional reference point R3 is reduced. In addition, although FIGS. 6 and 7 show a two-dimensional detection image for one marker, when a two-dimensional detection image is generated using a plurality of markers, an error of definition of the three-dimensional reference data may decrease and the accuracy may increase. That is, it is understood that FIGS. 6 and 7 show three detection images among a plurality of two-dimensional detected images and one of the plurality of markers.

Figure 8:
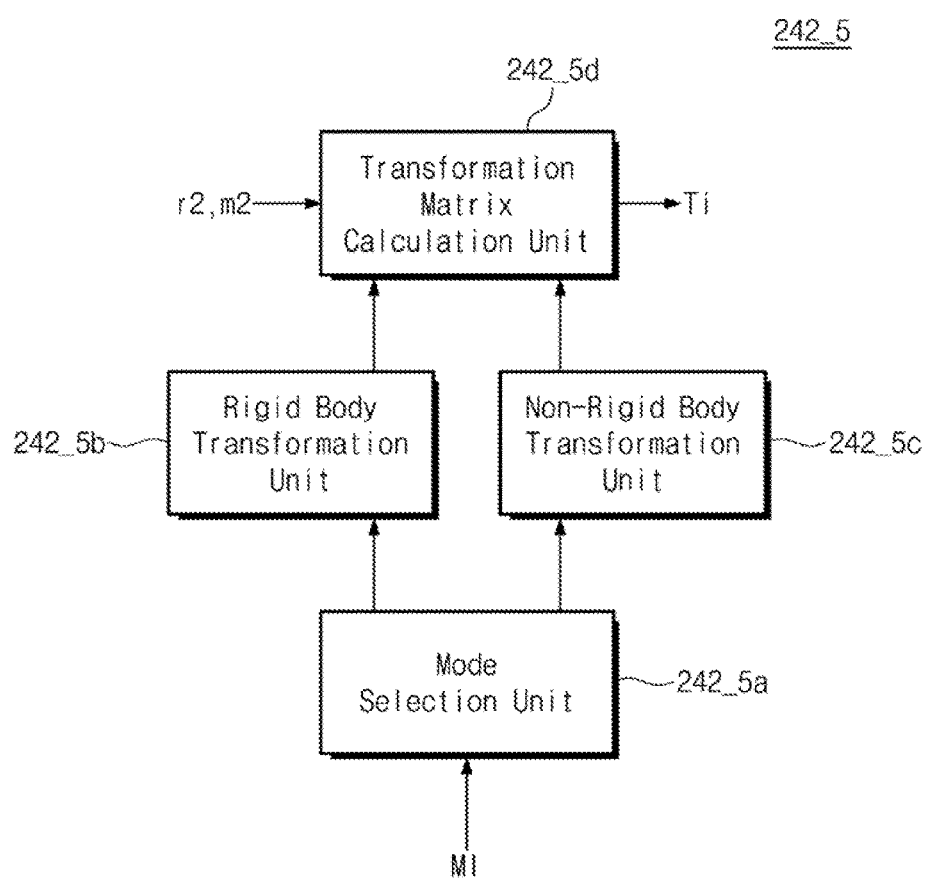
FIG. 8 is a block diagram of a comparator of FIG. 4.

FIG. 8 is a block diagram of the comparator 242_5 of FIG. 4.

Referring to FIG. 8, the comparator 242_5 includes a mode selection unit 242_5a, a rigid body transformation unit 242_5b, a non-rigid body transformation unit 242_5c, and a transformation matrix calculation unit 242_5d.

The mode selection unit 242_5a receives a mode selection signal MI. The mode selection signal MI may be a signal generated by the photographing device controller 210 based on a mode inputted by a user to the input unit 280 of FIG. 2. The mode selection signal MI is a signal for selecting one of a rigid body transformation mode or a non-rigid body transformation mode. The rigid body transformation mode is a mode for calculating a transformation matrix on the assumption that there is no motion of the subject. For example, when a subject with almost no involuntary movement, such as inanimate subjects or human legs, is photographed, the rigid body transformation mode may be used. The non-rigid body transformation mode is a mode for calculating the transformation matrix in consideration of the motion of the subject. For example, since movement by the lungs or the heart occurs during the photographing of the chest of a human body, the non-rigid body transformation mode may be used during the photographing of such a subject. The mode selection unit 242_5a may include a switch for selectively driving any one of the rigid body transformation unit 242_5b and the non-rigid body transformation unit 242_5c based on the mode selection signal MI.

The rigid body transformation unit 242_5b provides a rigid body transformation control signal to the transformation matrix calculation unit 242_5d when the comparator 242_5 operates in the rigid body transformation mode. The rigid body transformation mode may be a mode considering only the error of the movement trace of the gantry 100. Therefore, the rigid body transformation unit 242_5b controls the transformation matrix calculation unit 242_5d to generate the transformation matrix Ti under the assumption that there is no movement of the marker attached to the subject. For example, the difference between the target data m2 detected by the coordinate detection unit 242_2 in FIG. 4 and the two-dimensional reference data r2 generated through the first multiplication operator 242_4 is based on the moving path error of the gantry. As described above, the target data m2 and the two-dimensional reference data r2 exist as many as the number of markers formed on the subject in one two-dimensional detection image. Since the positional relationship between the markers attached to the subject is unchanged, the target data m2 corresponding to the attached markers and the two-dimensional reference data r2 are all determined as reliable data. Therefore, the rigid body transformation unit 242_5b controls the transformation matrix calculation unit 242_5d to calculate the cost function of Equation 2 by using the target data m2 corresponding to all the markers and the two-dimensional reference data r2.

The non-rigid body transformation unit 242_5c provides a non-rigid body transformation control signal to the transformation matrix calculation unit 242_5d when the comparator 242_5 operates in the non-rigid body transformation mode. The non-rigid body transformation mode may be a mode considering a movement of a subject in addition to the error of the movement trace of the gantry 100. Therefore, the non-rigid body transformation unit 242_5c controls the transformation matrix calculation unit 242_5d to generate the transformation matrix Ti by independently considering a marker attached to a moving area of the subject and a marker attached to a non-moving area. For example, the target data m2 corresponding to the markers attached to a region where the subject does not move and the two-dimensional reference data r2 are determined as reliable data, and the transformation matrix Ti is calculated in the same way as the rigid body transformation mode. The target data m2 corresponding to the markers attached to an area where the subject does not move and the two-dimensional reference data r2 are extracted separately, and the non-rigid body transformation unit 242_5c controls the transformation matrix calculation unit 242_5d to calculate the cost function for non-rigid body transformation separately.

The transformation matrix calculation unit 242_5d generates a corresponding transformation matrix Ti according to the rigid-body transformation mode or the non-rigid body transformation mode. The transformation matrix calculation unit 242_5d calculates the cost function by using the target data m2 corresponding to all the markers and the two-dimensional reference data r2 in the rigid body transformation mode. Therefore, the correction of the target data m2 for generating the three-dimensional reconstruction image data D13 may be performed collectively. For example, when the correction parameters of the target data m2 for one two-dimensional detection image are the X axis movement, the Y axis movement, the Z axis movement, the X axis rotation, the Y axis rotation, or the Z axis rotation, the amount of movement or the amount of rotation of the plurality of target data m2 corresponding to the target data m2 may be applied equally to each other.

The transformation matrix calculation unit 242_5d separately calculates the cost function for the target data m2 attached to an area where the subject moves and the two-dimensional reference data r2 in the non-rigid body transformation mode. Therefore, the correction of the target data m2 for generating the three-dimensional reconstruction image data D13 may be performed separately. For example, the movement amount or the rotation amount of the target data m2 corresponding to the non-moving markers are equal to each other, and the movement amount or the rotation amount of the target data m2 corresponding to the moving markers may be separately adjusted.

Figure 9:
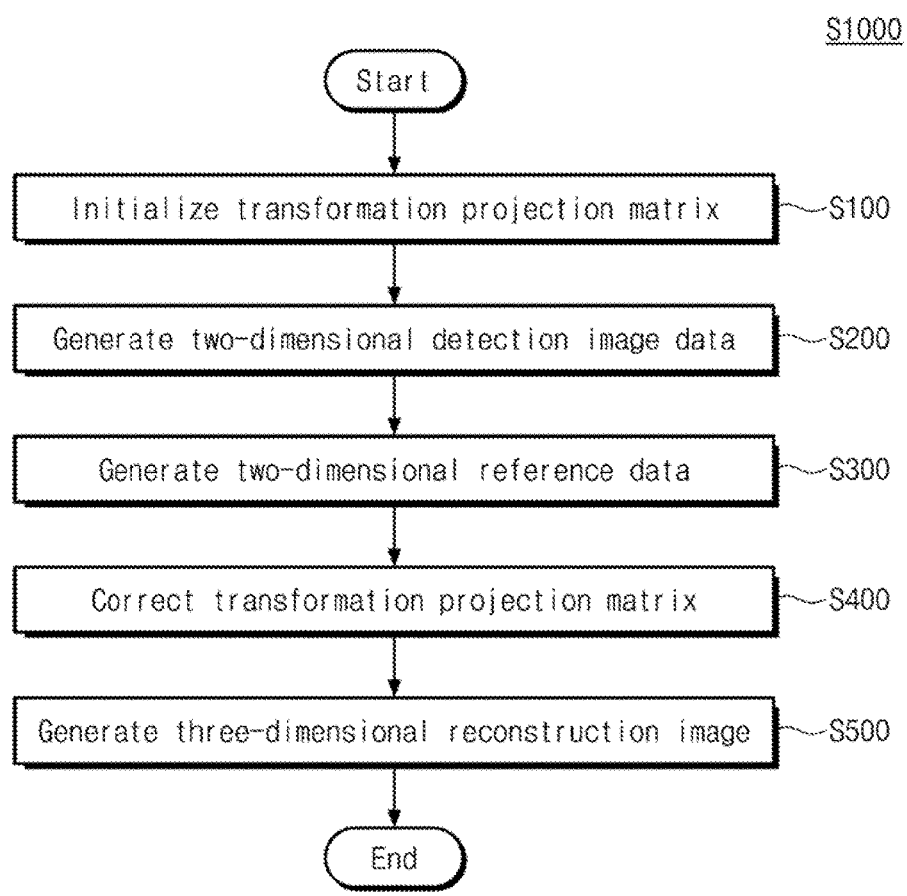
FIG. 9 is a flowchart of a computed tomography image correction method according to an embodiment of the inventive concept.
Figure 10:
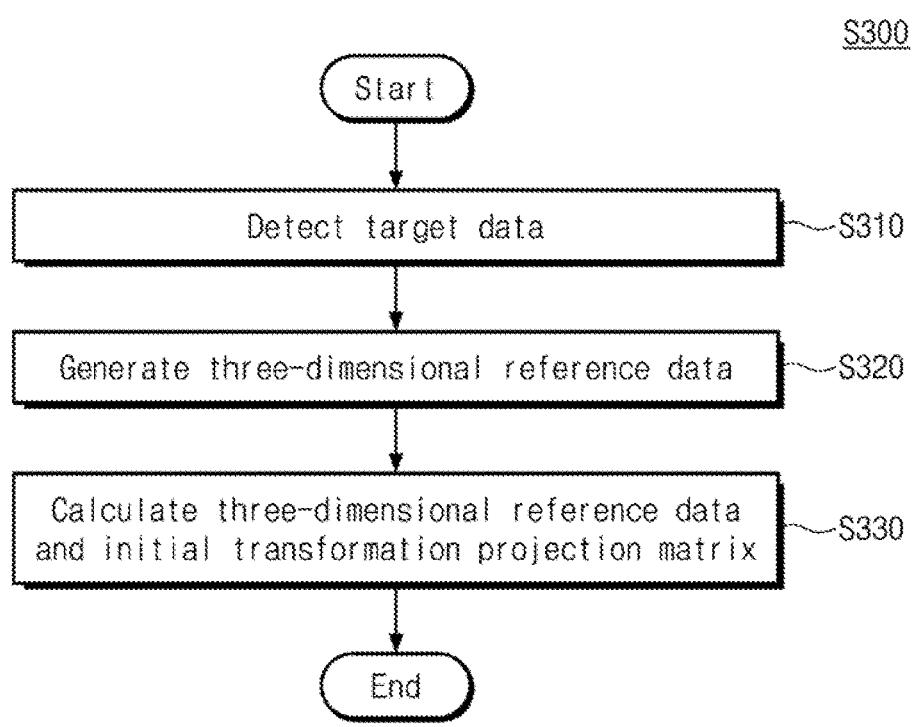
FIG. 10 is a flowchart illustrating the generating of two-dimensional reference data of FIG. 9.

FIG. 9 is a flowchart of a computed tomography image correction method according to an embodiment of the inventive concept. FIG. 10 is a flowchart illustrating the generating of two-dimensional reference data of FIG. 9.

Referring to FIG. 9, the computed tomography image correction method (S1000) includes initializing a transformation projection matrix (S100), generating two-dimensional detection image data (S200), generating two-dimensional reference data (S300), correcting the transformation projection matrix (S400), and generating a three-dimensional reconstruction image (S500). The computed tomography image correction method (S1000) is performed by the computed tomography devices 1000 of FIGS. 1 and 2. The initializing of the transformation projection matrix (S100), the generating of the two-dimensional detection image data (S200), the generating of the two-dimensional reference data (S300), the correcting of the transformation projection matrix (S400), and the generating of the three-dimensional reconstruction image (S500) are performed by the image processing processor 240 of FIG. 2.

The initializing of the transformation projection matrix (100) may be performed by the initialization unit 241 of FIG. 3. In the initializing of the transformation projection matrix (100), the image processing processor 240 initializes the transformation projection matrix value. For example, the image processing processor 240 may calculate a transformation projection matrix, assuming that the gantry 100 moves along an ideal circular trace, and also calculate a transformation projection matrix by using a correction phantom that accurately knows the three-dimensional coordinates.

The generating of the two-dimensional detection image data (S200) may be performed by the image correction unit 242 of FIG. 3. In the generating of the two-dimensional detection image data (S200), the gantry 100 photographs a subject to generate a two-dimensional detection image DI2. The subject may be attached with markers for identifying three-dimensional coordinates, and the two-dimensional detection image DI2 includes a target image corresponding to the markers. The image processing processor 240 converts the two-dimensional detection image DI2 to generate two-dimensional detection image data DID.

The generating of the two-dimensional reference data (S300) may be performed by the image correction unit 242 of FIG. 3. Referring to FIG. 10, the generating of the two-dimensional reference data includes detecting target data (S310), generating three-dimensional reference data (S320), and calculating an initial transformation projection matrix with the three-dimensional reference data (S330).

In the detecting of the target data (S310), the image processing processor 240 extracts the target data m2 from the two-dimensional detection image data DID. The target data m2 is the data in which the target image corresponding to the markers is converted. The target data m2 may include two-dimensional coordinate information of the target image.

In the generating of the three-dimensional reference data (S320), the image processing processor 240 generates the three-dimensional reference data r3 by performing a back projection operation on the target data m2. As described with reference to FIGS. 5 to 7, the image processing processor 240 extends a restoration line for the target data m2 corresponding to each marker, extracts the coordinates of the intersection points of the extended restoration lines to determine the average value of the intersection points as the coordinate information of the three-dimensional reference data r3.

In the calculating of the 3D reference data and the initial transformation projection matrix, the image processing processor 240 multiplies the 3D reference data r3 by the initialized transformation projection matrix. That is, the image processing processor 240 generates the two-dimensional reference data r2 by mapping the three-dimensional coordinate information included in the three-dimensional reference data r3.

The correcting of the transformation projection matrix (S400) may be performed by the image correction unit 242 of FIG. 3. In the correcting of the transformation projection matrix (S400), the image processing processor 240 generates a transformation matrix Ti based on the difference between the two-dimensional reference data r2 and the target data m2. The image processing processor 240 multiplies the transformation matrix Ti and the initialized transformation projection matrix to generate a corrected transformation projection matrix Pu. The image processing processor 240 may operate in a rigid body transformation mode on the assumption that there is no motion of the subject to generate the transformation matrix Ti using the target data m2 for all the markers. Alternatively, the image processing processor 240 may operate in a non-rigid body transformation mode on the assumption that there is a movement of the subject to generate the transformation matrix Ti by separately calculating the target data m2 for all the moving markers.

The generating of the three-dimensional reconstruction image (S500) may be performed by the three-dimensional image generation unit 244 of FIG. 3. In the generating of the three-dimensional reconstruction image (S500), the image processing processor 240 reconstructs the two-dimensional detection image data DID into the three-dimensional reconstruction image data DI3 using the corrected transformation projection matrix Pu.

A computed tomography device and a computed tomography image correction method using the same according to an embodiment of the inventive concept may provide a stable three-dimensional reconstruction image by correcting a transformation projection matrix according to a gantry movement path.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:

1. A computed tomography device comprising:
a gantry comprising a light source for irradiating light, a detector disposed facing the light source and for receiving the light, and an arm for supporting the light source and the detector;
an image processing processor configured to receive a two-dimensional detection image for a subject from the detector to convert the received two-dimensional detection image to two-dimensional detection image data, generate two-dimensional reference data based on the two-dimensional detection image data and an initial transformation projection matrix, generate a corrected transformation projection matrix based on a difference between the two-dimensional reference data and the two-dimensional detection image data, and generate three-dimensional reconstruction image data based on the two-dimensional detection image data and the corrected transformation projection matrix;
a body portion configured to support the arm, and accommodate the image processing processor; and
a moving portion configured to be connected to the body portion.

2. The device of claim 1, wherein
the image processing processor generates the initial transformation projection matrix for mapping coordinates of the subject according to a movement path of the gantry to two-dimensional coordinates, generates three-dimensional reference data by performing a back projection operation on the two-dimensional detection image data, and generates the two-dimensional reference data based on the three-dimensional reference data and the initial transformation projection matrix.

3. The device of claim 2, wherein
the gantry photographs a correction phantom including a plurality of markers; and
the image processing processor generates an initial transformation projection matrix based on three-dimensional coordinates of the correction phantom and a two-dimensional detection image of the correction phantom.

4. The device of claim 2, wherein the image processing processor generates an initial transformation projection matrix based on a theoretical value of a movement trace of the arm.

5. The device of claim 2, wherein the gantry photographs the subject where a marker is disposed to generate the two-dimensional detection image; and
the two-dimensional detection image comprises a target image corresponding to the marker.

6. The device of claim 5, wherein the marker comprises a plurality of markers,
the image processing processor operates in one of a rigid body transformation mode and a non-rigid body transformation mode,
in the rigid body transformation mode, the corrected transformation projection matrix is generated so that correction amounts of target images corresponding to the plurality of markers are equal to each other, and
in the non-rigid body transformation mode, the corrected transformation projection matrix is generated so that correction amounts of target images corresponding to a part of the plurality of markers are different from correction amounts of target images corresponding to the rest of the plurality of markers.

7. The device of claim 6, wherein the plurality of markers are disposed on the subject so that less than three markers are formed with respect to an arbitrary line projecting the subject.

8. The device of claim 5, wherein the two-dimensional detection image comprises a plurality of two-dimensional detection images, and the gantry continuously photographs the subject while moving along a movement trace to generate the plurality of two-dimensional detection images.

9. The device of claim 8, wherein the image processing processor determines a plurality of restoration lines contacting three-dimensional coordinates of the target images based on target images corresponding to the plurality of two-dimensional detection images and an irradiation direction of the light, and generates the three-dimensional reference data based on intersection points between the restoration lines.

10. The device of claim 9, wherein the three-dimensional reference data is an average value of the intersection points.

11. The device of claim 9, wherein the plurality of restoration lines are generated by a back projection operation based on the target image and the initial transformation projection matrix.

12. The device of claim 5, wherein the image processing processor generates the two-dimensional reference data by multiplying the three-dimensional reference data and the initial transformation projection matrix.

13. The device of claim 5, wherein the image processing processor extracts target data corresponding to the target image from the two-dimensional detection image data.

14. The device of claim 13, wherein the image processing processor generates a transformation matrix based on a cost function that minimizes a difference between coordinate information of the two-dimensional reference data and coordinate information of the target data, and multiples the transformation matrix and the initial transformation projection matrix to generate the corrected transformation projection matrix.

15. The device of claim 2, wherein the image processing processor comprises:
a modulator configured to convert the two-dimensional detection image into two-dimensional detection image data;

a coordinate detection unit configured to receive the two-dimensional detection image data from the modulator to generate target data;

a back projection operator configured to receive the target data to generate the three-dimensional reference data;

a first multiplication operator configured to multiply the three-dimensional reference data and the initial transformation projection matrix to generate the two-dimensional reference data;

a comparator configured to compare the two-dimensional reference data and the target data to generate a transformation matrix; and a second multiplication operator configured to multiply the transformation matrix and the initial transformation projection matrix to generate the corrected transformation projection matrix.

16. The device of claim 15, wherein the image processing processor further comprises a three-dimensional image generation unit for generating the three-dimensional reconstruction image based on the two-dimensional image data and the corrected transformation projection matrix.

17. The device of claim 16, wherein the image processing processor further comprises a memory unit for storing the initial transformation projection matrix or the corrected transformation projection matrix, and the three-dimensional image generation unit receives the corrected transformation projection matrix value from the memory unit.

18. The device of claim 1, further comprising:

a light source control unit configured to control a light amount, a light angle, or a light irradiation time of the light source;

an arm control unit configured to control a movement amount or a movement speed of the arm; and a photographing device controller configured to provide a control signal to the light source control unit, the arm control unit, and the image processing processor.

19. A computed tomography image correction method comprising:

initializing a transformation projection matrix for mapping coordinates of a subject to two-dimensional coordinates;

photographing the subject with a gantry to generate two-dimensional detection image data including target data;

generating three-dimensional reference data by performing a back projection operation on the target data, and generating two-dimensional reference data by mapping coordinate information of the three-dimensional reference data to the initialized transformation projection matrix;

correcting the transformation projection matrix based on a difference between the two-dimensional reference data and the target data; and generating a three-dimensional reconstruction image based on the corrected transformation projection matrix.

20. The method of claim 19, wherein the generating of the two-dimensional reference data comprises:

detecting the target data from the two-dimensional detection image data;

generating the three-dimensional reference data from the target data; and calculating the three-dimensional reference data and the initialized transformation projection matrix.

\* \* \* \* \*